(12) United States Patent
Hay et al.

(10) Patent No.: US 8,548,122 B2
(45) Date of Patent: Oct. 1, 2013

(54) METHOD AND APPARATUS FOR GENERATING MULTIPLE STUDIES

(75) Inventors: Ori Hay, Haifa (IL); Shlomo Gotman, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 1353 days.

(21) Appl. No.: 11/997,654

(22) PCT Filed: Jul. 27, 2006

(86) PCT No.: PCT/IB2006/052580
§ 371 (c)(1),
(2), (4) Date: Feb. 1, 2008

(87) PCT Pub. No.: WO2007/015196
PCT Pub. Date: Feb. 8, 2007

(65) Prior Publication Data
US 2008/0234571 A1    Sep. 25, 2008

Related U.S. Application Data

(60) Provisional application No. 60/595,760, filed on Aug. 3, 2005.

(51) Int. Cl.
*A61B 6/00* (2006.01)
(52) U.S. Cl.
USPC .......................................................... 378/62

(58) Field of Classification Search
USPC . 600/407, 425–429, 408, 409; 382/128–133, 382/156, 162, 169, 172, 194, 196, 203, 209, 382/232, 237, 240, 243, 248, 260, 268–295, 382/302; 378/37, 28, 62, 83; 707/102; 356/443; 250/453.11; 78/94
See application file for complete search history.

(56) References Cited

U.S. PATENT DOCUMENTS

| | | | |
|---|---|---|---|
| 6,678,399 B2 * | 1/2004 | Doi et al. | 382/131 |
| 2002/0085026 A1 | 7/2002 | Bocionek et al. | |
| 2004/0068167 A1 * | 4/2004 | Hsieh et al. | 600/407 |
| 2004/0101179 A1 * | 5/2004 | Suryanarayanan et al. | 382/128 |
| 2004/0128164 A1 | 7/2004 | DeJarnette et al. | |
| 2004/0171931 A1 | 9/2004 | Barth et al. | |
| 2005/0135549 A1 | 6/2005 | Hagiwara | |

FOREIGN PATENT DOCUMENTS

| | | |
|---|---|---|
| DE | 10065345 A1 | 7/2001 |
| EP | 0983747 A1 | 3/2000 |

* cited by examiner

*Primary Examiner* — Elmer Chao (57) ABSTRACT

Information indicative of multiple regions of the anatomy of a patient (602, 604, 606), such as one or more of the head, neck, chest, abdomen, or pelvis, is obtained in a single scan. A plurality of studies (32) are generated. Each study definition includes a region of the patient's anatomy (602, 604) and a study protocol. Each study (32) includes (48) images generated using information from the scan and the value of the imaging parameter.

15 Claims, 4 Drawing Sheets

METHOD AND APPARATUS FOR GENERATING MULTIPLE STUDIES

CROSS REFERENCE TO RELATED APPLICATIONS

This application claims the benefit of U.S. provisional application Ser. No. 60/595,760 filed Aug. 3, 2005, which is incorporated herein by reference.

The present invention relates to the field of medical imaging, and particularly to techniques for generating multiple studies or series from data obtained during a scanning procedure. It will be appreciated, however, that the invention finds applicability to other fields such as the imaging of animals, non-medical imaging, and industrial inspection.

Computed tomography (CT) and other imaging scanners are well suited to obtaining information indicative of the internal characteristics of an object under examination, for example the internal anatomy of a human patient. With continuing advances in scanning technology, these devices have been increasingly able to scan relatively larger areas of a patient in a given period of time and to generate ever increasing numbers of images and other information. Moreover, advances in technology have also allowed greater flexibility in selecting the type and formats of the images to be generated and displayed.

Scanners are commonly used to generate image data indicative of a region of the patient's anatomy, for example of the head, neck, chest, abdomen, or pelvis. In some cases, it is necessary to obtain information about multiple regions of the patient's anatomy. In that case, the images and other information regarding the various regions may be used by different persons or for different purposes, some or all of which may have different needs.

Each region of the patient's anatomy can be scanned in a separate scanning procedure. Doing so provides flexibility in defining scanning and imaging parameters and storing and communicating the results of the scan, and also allows for relatively faster processing of only the region of interest. At the same time, however, conducting multiple scanning procedures on a particular patient can have various drawbacks, such as being inconvenient to the patient and relatively time consuming.

Multiple regions of a patient's anatomy may also be scanned in a single scanning procedure. Doing so can be relatively more convenient for the patient and also more time efficient. At the same time, however, scanning multiple regions of the patient in a single scan has heretofore offered relatively little flexibility in defining scanning and imaging parameters, storing and communicating the scan results, and has required the relatively cumbersome processing of large data sets.

Accordingly, it would be desirable to scan multiple regions of the patient's anatomy in a single scan while also accommodating the differing imaging and other requirements for each region. Aspects of the present invention address these matters, and others.

According to a first aspect of the present invention, a method of generating a plurality of studies using information from an imaging scan of a patient's anatomy includes defining at least first and second studies. Each study definition includes a region of the patient's anatomy and a study protocol. The method also includes using the corresponding study protocol and information from the imaging scan to generate each of the studies. Each study includes images indicative of the interior of the anatomy of the patient in the corresponding region of the patient's anatomy. The method also includes storing the studies in a computer readable storage medium.

According to a more limited aspect of the invention, the method also includes using information from the imaging scan to define first and second regions of the patient's anatomy.

According to a yet more limited aspect, the method includes using information from the imaging scan to generate volumetric data indicative of the patient's anatomy.

The step of using information from the imaging scan to define the regions includes classifying the volumetric data into a plurality of categories, using morphological knowledge of the patient's anatomy, and evaluating the cross sectional area of the patient's anatomy.

According to another more limited aspect of the invention, the first study protocol includes a first reconstruction protocol and the second study protocol includes a second reconstruction protocol.

According to a still more limited aspect of the invention, the first study protocol includes a first display protocol and the second study protocol includes a second display protocol.

According to another limited aspect of the invention, the method also includes using information from a localizer scan to define the regions.

According to another more limited aspect, the localizer scan is a surview scan. The localizer scan may also be a volumetric scan.

According to yet another more limited aspect of the invention, the method includes using information from the localizer scan to define the regions includes locating the patient's lungs, pelvis bone, and diaphragm.

According to yet another more limited aspect of the invention, the first and second studies each include an overview image of the first and second regions of the patient's anatomy and an identifier which uniquely identifies the study. The first and second regions are indicated on the overview image.

According to yet another more limited aspect of the invention, the first study protocol includes a first reconstruction protocol and the second study protocol includes a second reconstruction protocol.

According to another limited aspect of the invention, the first and second regions overlap.

According to another limited aspect of the invention, the method includes receiving a request for a first study of a first requested region of the patient's anatomy and a request for a second study of a second requested region of the patient's anatomy, and defining an extent of the imaging scan. The extent includes the first and second requested regions of the patient's anatomy.

According to still another limited aspect of the invention, the method includes notifying a computer information system that the first and second studies have been generated.

According to another aspect of the present invention, a method includes analyzing information from a scan of at least first and second regions of the anatomy of a patient to determine a location of the first and second regions in the scan data, using a first study protocol and information from the scan to generate an image indicative of the interior anatomy of the patient in the first region, using a second study protocol and information from the scan to generate an image indicative of the interior anatomy of the patient in the second region, and storing the images in a computer readable storage medium.

According to a limited aspect of the invention, the step of analyzing includes analyzing information from a scan of at least first, second, and third regions of the anatomy of a patient to determine a location of the first, second and third regions in the scan data. The method also includes using a third study protocol and information from the scan to generate an image indicative of the interior anatomy of the patient in the third region.

According to a limited aspect of the invention, the method includes receiving a request for a first study of the first region and a request for a second study of the second region and obtaining a scan of at least the first and second regions.

According to a more limited aspect of the invention, the requests are received from a computer information system.

According to another limited aspect of the invention, the step of storing includes storing the images as separate studies.

According to another limited aspect of the invention, the method includes reporting to a computer information system that the first and second studies have been generated.

According to another limited aspect of the invention, the step of using a first study protocol includes using a first reconstruction protocol and the step of using a second study protocol includes using a second reconstruction protocol. The first and second reconstruction protocols each may include at least one of matrix size and field of view.

According to another limited aspect of the invention, the step of using a first study protocol includes using a first display protocol and the step of using a second study protocol includes using a second display protocol.

According to a more limited aspect of the invention, the scan is a computed tomography scan and the step of analyzing includes analyzing image data.

According to another aspect of the invention, an imaging method includes obtaining a first scan which provides information indicative of the interior anatomy of a patient. The information from the second scan includes information indicative of at least first and second regions of the patient's anatomy. The method also includes using information from the first scan to determine a location of the first and second regions, obtaining a second scan which provides information indicative of the interior anatomy of a patient in at least the first and second regions, using a first study protocol and information from the second scan to generate at least a first image indicative of the interior anatomy of the patient in the first region, using a second study protocol and information from the second scan to generate at least a first image indicative of the interior anatomy of the patient in the second region, and storing the images in a computer readable storage medium.

According to more limited aspect of the invention, the first scan provides volumetric information indicative of the interior anatomy of the patient. The first scan may be a relatively low dose helical computed tomography scan.

According to another limited aspect of the invention, the step of using a first study protocol includes using a first scan protocol and the step of using a second study protocol includes using a second scan protocol. The scan may be a computed tomography scan and the first and second scan protocols may each include x-ray tube voltage and current.

According to another aspect of the invention, an apparatus for generating a plurality of studies using information from an imaging scan includes means for defining a first study, the first study definition including a first region of the patient's anatomy and a first study protocol, means for defining a second study, the second study definition including a second region of the patient's anatomy and a second study protocol, means for generating the first and second studies, wherein the first and second studies each include images indicative of the interior anatomy of the patient in the corresponding region, and wherein the images are generated using information from the imaging scan and using the corresponding study protocol, and a computer readable storage medium for storing the studies.

Figure 1:
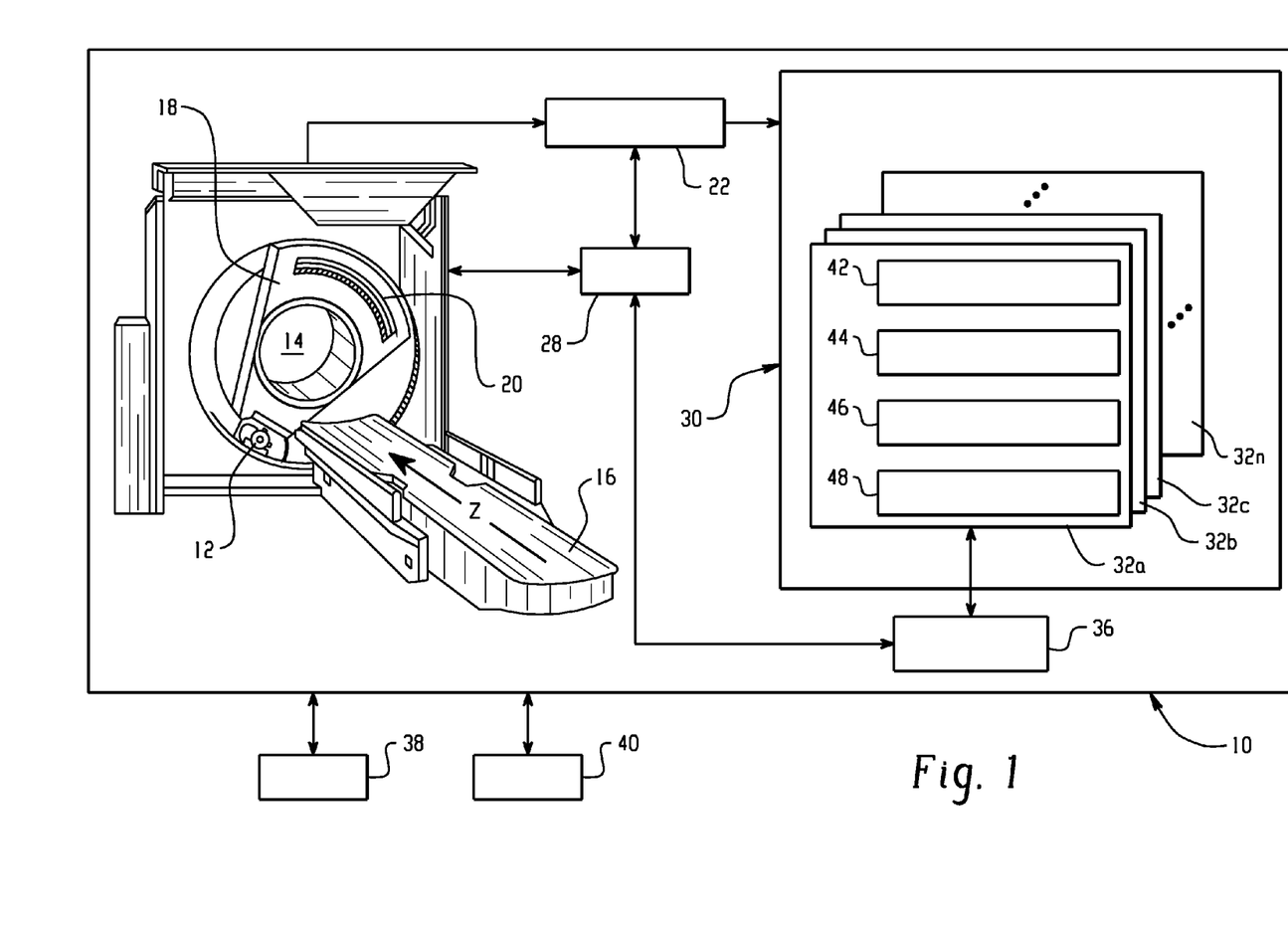
FIG. 1 depicts a CT scanner.

With reference to FIG. 1, a computed tomography (CT) scanner 10 includes a rotating gantry 18 which rotates about the z-axis. The gantry 18 supports an x-ray source 12 such as an x-ray tube. The gantry 18 also supports an x-ray sensitive detector 20 which subtends an angular arc on the opposite side of an examination region 14. X-rays produced by the x-ray source 12 traverse the examination region 14 and are detected by the detector 20.

In one embodiment, the detector 20 is a multi-slice detector which includes more than one row of detectors extending in the z-direction. Flat panel or other detector 20 configurations may also be implemented. Depending on the configuration of the detector 20, the x-ray source 12 generates a generally fan, wedge, or cone shaped radiation beam. Moreover, a so-called fourth generation scanner configuration, in which the detector 20 spans an arc of 360 degrees and remains stationary while the x-ray source 12 rotates, may also be implemented.

A patient support 16 such as a couch supports the patient in the examination region 14. The patient support 16 is preferably movable in the z-direction. A controller 28 coordinates the various scan parameters as necessary to carry out a desired scan protocol. In a helical scan, movement of the support 16 and the gantry 18 are coordinated along with such that the x-ray source 12 and the detectors 20 traverse a generally helical path with respect to the patient. In a surview scan, the movement of the support 16 and the gantry are coordinated such that the x-ray source 12 and the detectors traverse a generally linear path with respect to the patient, for example to provide an anterior-posterior or a lateral view of the patient.

Data collected by the detector 20 are processed by a reconstructor 20 to generate volumetric data indicative of the interior anatomy of the patient. The images are stored in a suitable memory 30 such as a computer disk, other volatile or non-volatile memory or other memory storage device. The memory 30 is organized to store data indicative of a number of image series or studies 32a, 32b, 32c . . . 32n. Associated with each study 32 are a unique identifier such as a study or accession number 42, patient information 44, and localizer 46 and diagnostic 48 images. In this regard, it should be noted that the data associated with each series need not be in separate memory locations. Rather, the data may be arranged in suitable data structures and accessed using associated pointers, linked lists, or the like.

Images and other information generated from the data obtained by the scanner are further manipulated by one or more imaging computers or workstations 36, which may also be used as the scanner console. The imaging computers or workstations 36 typically include an operator interface having an output device such as a human readable display and/or film printer and an input device such as a keyboard and/or mouse. Thus, the operator may view and manipulate images, select desired scan protocols, initiate or terminate scans, and otherwise interact with the scanner 10.

The scanner 10 may also be in operative communication with a computer information system such as one or both of a hospital information system/radiology information system (HIS/RIS) 38 or picture archiving and communication system (PACS) system 40, over a HL-7, DICOM or other suitable interface.

Figure 2:
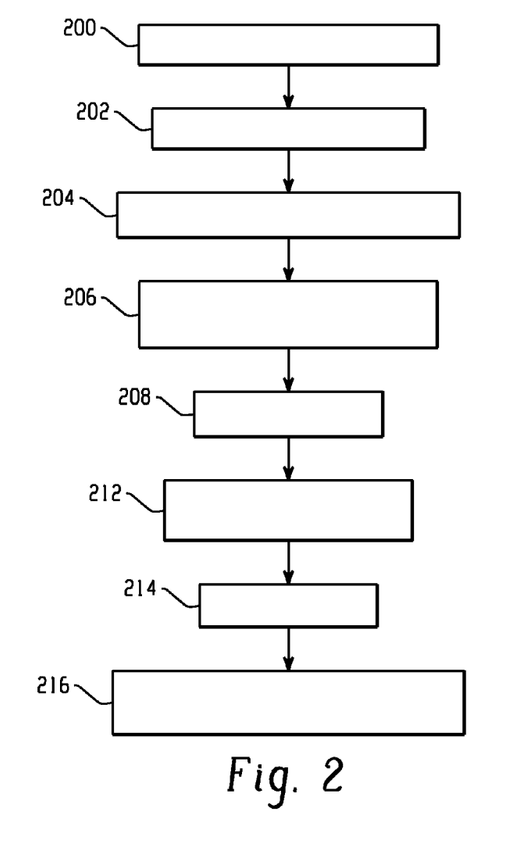
FIG. 2 depicts a first technique for using information from a scan to generate a plurality of studies.

Turning now to FIG. 2, a technique for using information from a CT scan to generate a plurality of studies or image series will be described. At 200, imaging requests are transferred from the computer information system such as the hospital HIS/RIS system 38 and received by the CT scanner 10. The imaging requests may include requests for separate scans that may be advantageously acquired in a single scan or requests to scan multiple regions for which there may be different informational requirements, for example requests covering one or more regions of the body such as the head, neck, chest, abdomen, or pelvis. Alternately, imaging requests may be entered manually by the operator through the operator interface or otherwise.

The CT scanner combines multiple procedure requests from the HIS/RIS system into one scan automatically based on internal rules and predefined protocols. Thus, for example, these rules my combine requests for separate study conveying the chest, abdomen, and pelvis into a single scan, with each study being generated according to a predefined study protocol. Alternatively, the operator can combine the requests manually. Another method may include a predefined request from the HIS/RIS system to be interpreted as a single scan that has to be split into multiple studies or series by the scanner (either automatically or manually).

At 202, a volumetric localizer scan of the patient is obtained. The localizer scan is preferably a relatively low dose or relatively fast, high pitch helical scan of the patient which provides information of a quality sufficient for localization purposes but which may not be optimal for diagnostic purposes. Similarly, the reconstruction protocol is preferably selected to provide a relatively faster reconstruction time. The axial extent of the localizer scan corresponds approximately to the axial extent of the requested procedures. Alternately, the localizer scan may be a surview scan.

At 204, information from the localizer scan is used to identify the relevant regions of the patient's anatomy. The regions correspond to the regions of the requested procedures.

At 206, a diagnostic quality CT scan which includes the relevant regions of the patient's anatomy is planned, and the desired studies are defined.

The identified anatomical regions are used to establish a region of interest for each of two or more studies. In the example of FIG. 4*b*, the location of region of interest for three studies—a first study 602 in which the region of interest includes the patient's chest, a second study 604 in which the region of interest includes the patient's abdomen, and a third study 606 in which the region of interest includes the patient's pelvis—is depicted.

As shown in FIG. 4*b*, the region of interest of the first study 602 overlaps with the region of interest of the second study 604, which in turn overlaps with the region of interest of the third study 606. Thus, portions of the patient's anatomy may be included in more than one study, with images or other information being generated according to the protocol corresponding to each study. As will also be appreciated, there may be situations where it is desirable to arrange the regions of interests of the studies so that they do not overlap or so that there are gaps between them.

Again with reference to FIG. 4*b*, an overview image 600 such as a maximum intensity projection (MIP) anterior posterior view or the patient's interior anatomy is generated from the localizer data and displayed on the operator interface, with the regions of interest 602, 604, 606 of the respective studies indicated on the overview image 600. Of course, other views, such as lateral views, volume visualized views, and the like, may also be displayed. The user may be afforded an opportunity to review and alter the region of interest definitions using the operator interface. Alternately, the definition of the regions of interest may proceed automatically without input from the operator.

While the above description has focused on a graphic display, the region of interest for the various studies can also be described in other ways. For example, the regions of interest can be described numerically with reference to the distance from a location on the patient support 16, a location on the patient's anatomy, a coordinate in image space, the slice number, or the like.

Depending on the regions of interest, the purposes for which the study is being performed, user requirements and preferences, and the like, it is sometimes desirable to establish different study protocols for one or all of the studies 602, 604, 606. Thus, for example, it may be desirable for each study to have a unique reconstruction protocol in which different values are established for one or more parameters related to image reconstruction (such as reconstruction filters, slice thicknesses, fields of view, or matrix sizes). Similarly, it may be desirable for each study to have its own display protocol in which the format and other characteristics of the resulting images (such as axial, coronal, sagittal, multiplanar reformatted (MPR), MIP, or three dimensional rendered images, rendering parameters, coloration, or other information) are different. Moreover, it may be desirable for each study to have a different scan protocol in which different values are established for one or more parameters relating to the scanning operation (such as x-ray source 12 voltage or current, scan pitch, or collimation settings, in the case of a CT scanner).

In one embodiment, a default protocol is established for each study based on the region of interest of the study, the person requesting it, or other relevant characteristic. Thus, for example, the protocols used to generate images of the head, neck, and chest or requested by a different physician or physician group may have different default values. In another embodiment, some or all of the protocol information is entered by the operator. In another embodiment, the imaging request received from the computer information system would be used to establish the some or all of the protocol parameter values. Other or different parameters, or differing combinations of them, can also be implemented depending on the type or characteristics of a particular scanner or the requirements of a particular application.

Returning to FIG. 2, at 208, a diagnostic CT scan covering the desired regions of the patient's anatomy is obtained. In the example described above, the axial extent of the scan would include the patient's chest, abdomen, and pelvis. However, the scan need not be continuous over the patient's anatomy. In cases where there are gaps between the studies or the requested procedures, there may be corresponding gaps in the regions covered by the scan.

At 212, information from the diagnostic scan is used to generate the diagnostic image or images corresponding to each study, based on the study protocol established for each study.

At 214, the information associated with each study is stored in memory 30. With reference to FIG. 1, a unique identifier such an accession number 42, together with the relevant patient information 44, localizer image(s) 46, and diagnostic image(s) 48 are associated with each study 32*a*, 32*b*, 32*c* . . . 32*n*.

Returning now to FIG. 2, at 216, the studies are sent to a computer information system such as the PACS system 40 and a HIS/RIS or computer information system is notified that the studies corresponding to the requested procedures have been generated.

While the steps of generating the images corresponding to each study 212, storing the studies 214, and sending the studies to an information system are described serially, these steps may also be performed either partially or completely in parallel. Thus, for example, the information associated with a first study can be generated, stored, and sent to the information system before processing the next study, and so on.

Figure 3:
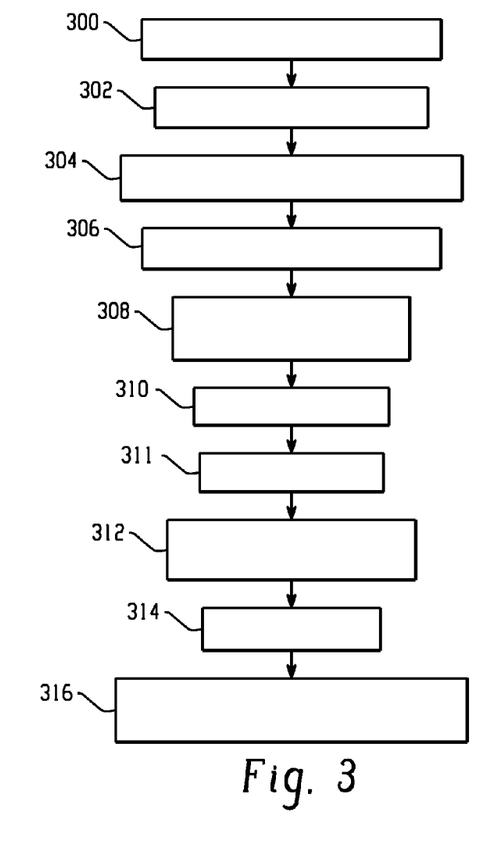
FIG. 3 depicts a second technique for using information from a scan to generate a plurality of studies.

Turning now to FIG. 3, another technique for using information from a CT scan to generate a plurality of studies or image series will be described. At 300, imaging requests are transferred from a computer information system such as the hospital HIS/RIS system 26 and received by the CT scanner 10. Alternately, such requests may be entered manually by the operator through the operator interface or otherwise.

At 302, a localizer scan of the patient is obtained and data reconstructed. The localizer scan is preferably a relatively low dose surview scan providing a two dimensional anterior-posterior and/or lateral view of the patient. The localizer scan provides information of a quality sufficient for localization purposes but which may not be optimal for diagnostic purposes. The axial extent of the localizer scan corresponds approximately to the axial extent of the requested procedures. Alternately, the localizer scan may be a low dose helical scan of the patient which provides volumetric information about the patient's anatomy.

At 304, the operator uses the CT information from the localizer scan to establish the scan bounds for a diagnostic quality scan (e.g., the scan staring location and end location, as well as the scan field of view) which encompasses the relevant regions of interest. In this regard, it is not necessary for the operator to establish bounds for each region of interest, but rather the extent of the scan as a whole.

At 306, a diagnostic quality CT scan which includes the relevant regions of the patient's anatomy is planned.

Figure 5:
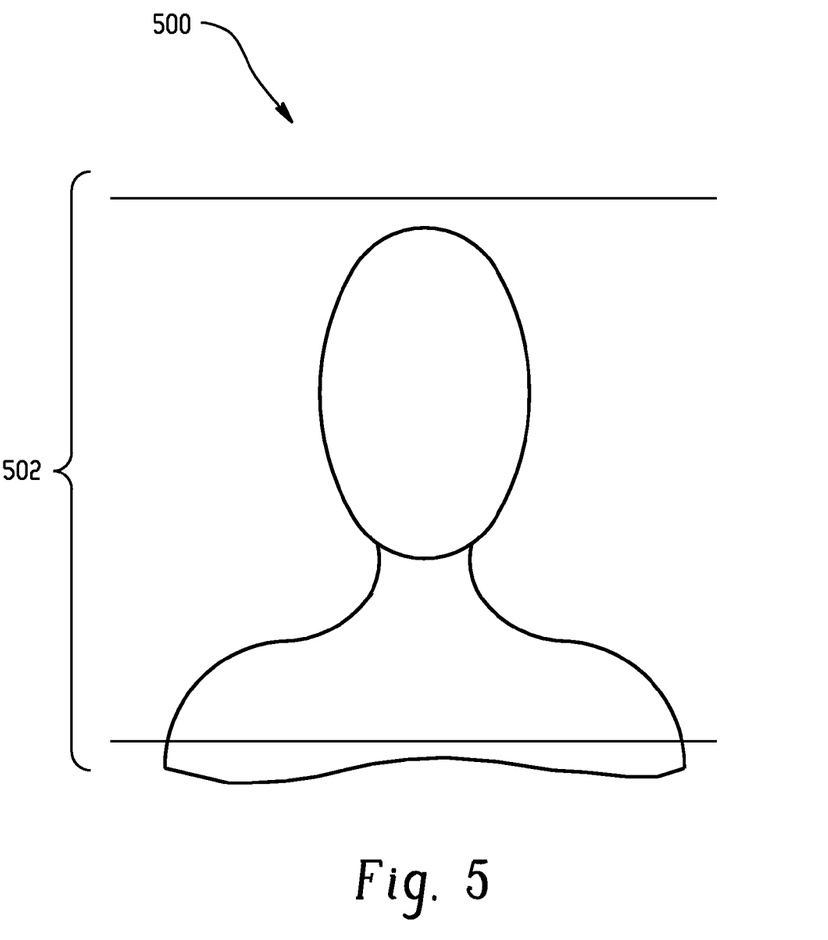
FIG. 5 depicts an exemplary image for planning a scan.

As shown schematically in FIG. 5, an overview image 500 such as a maximum intensity projection (MIP) anterior posterior view or the patient's interior anatomy is generated from the localizer data and displayed on the operator interface, with the regions of interest 502 to be covered by the scan indicated on the overview image 500. In the example of FIG. 5, the region 502 includes the patient's head and neck. It should be noted that, depending on the regions of interest, the scan may cover more than one non-contiguous region. Of course, other views, such as lateral views, volume visualized views, and the like, may also be displayed. The user may be afforded an opportunity to review and alter the axial extent of the scan using the operator interface. Alternately, the scan extent may be established automatically without operator review or feedback.

While the above has been described graphically, the region to be covered by the scan may also be depicted in other ways. For example, the locations can be depicted numerically with reference to the distance from a location on the patient support 16, a location on the patient's anatomy, the slice number, or the like.

A scan protocol is also established for the scan.

Returning to FIG. 3, a diagnostic CT scan covering the desired region of the patient's anatomy is obtained at 308. In the example described above, the axial extent of the scan would include the patient's head and neck. Again, however, the scan need not be continuous over the patient's anatomy. In cases where there are gaps between relevant regions, there may be corresponding gaps in the data collected by the scan. The data from the scan is reconstructed to create volumetric data indicative of the patient's interior anatomy, preferably using a reconstruction protocol selected to provide a relatively faster reconstruction time. This reconstruction provides information of a quality sufficient for localization purposes but which may not be optimal for diagnostic purposes.

At 310, information from the CT scan obtained at step 308 is analyzed to identify the relevant regions of the patient's anatomy. The relevant regions may also be identified based on the images generated from the volumetric data as they evolve during the course of an ongoing reconstruction.

At 311, the regions of the anatomy identified in step 308 are used to define multiple studies or series as generally described above in connection with step 206. Following the example of FIG. 5, two studies—a first study in which the region of interest includes the patient's head, and a second study in which the region of interest includes the patient's neck, would be defined. Of course, studies similar to those defined in the example of FIG. 4, or other desired studies, could also be defined.

At 312, information from the diagnostic scan is used to generate one or more diagnostic images corresponding to each study, based on the study protocol established for each study. Thus, each study may have different parameters (filters, rendering modes, 3D displays, etc.).

At 314, information associated with each study is stored in memory 30. With reference to FIG. 1, a unique identifier such as an accession number 42, together with the relevant patient information 44, localizer image(s) 46, and diagnostic image(s) 48 are associated with each study 32*a*, 32*b*, 32*c* . . . 32*n*.

Returning to now to FIG. 3, at 314, the studies are sent to a computer information system such as the PACS system 40, and a HIS/RIS or other computer information system is also notified that studies corresponding to the multiple requested procedures have been generated.

With reference to FIG. 4, the identification of the relevant regions of the patient's anatomy will now be described in greater detail. The volumetric data generated by a scan can be classified into a plurality of categories. The results of the classification, the calculation of the cross section of the patient's anatomy as a function of axial position, and morphological knowledge can be used to automatically identify regions of the anatomy.

Figure 4A:
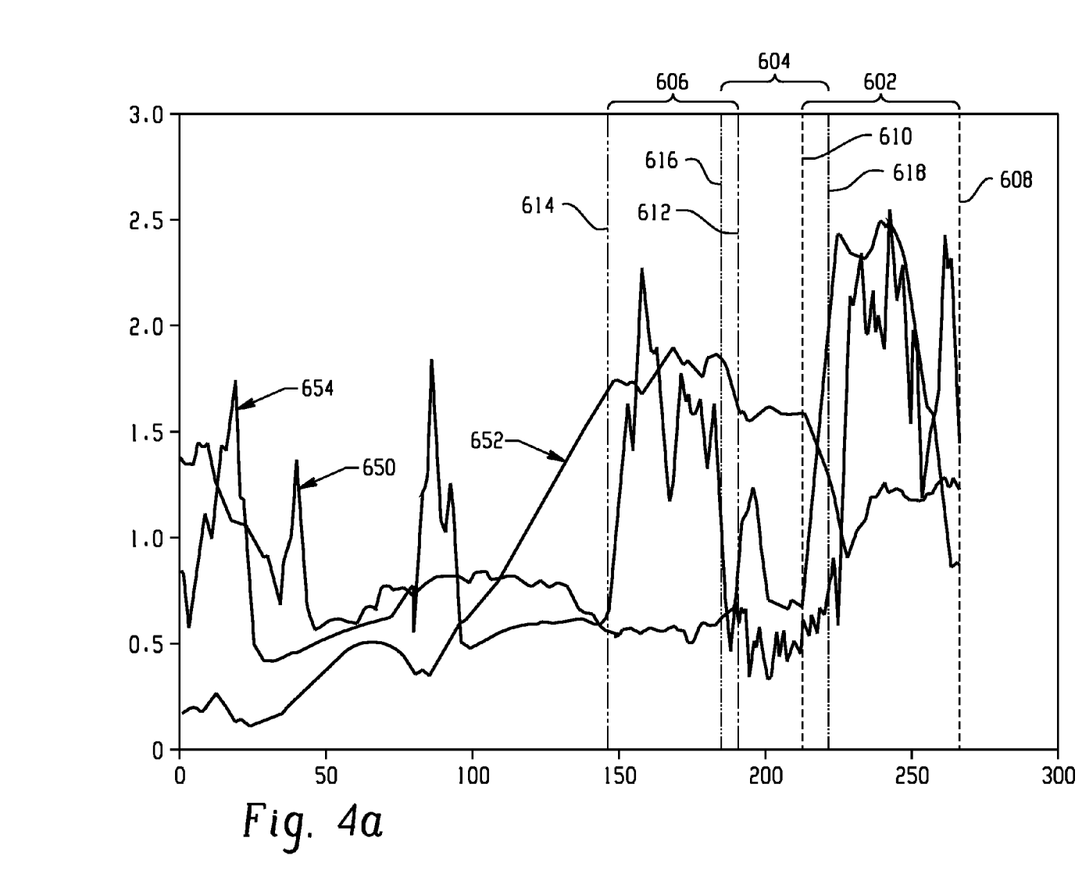
FIG. 4 depicts an exemplary histogram and region of interest definition.
Figure 4B:
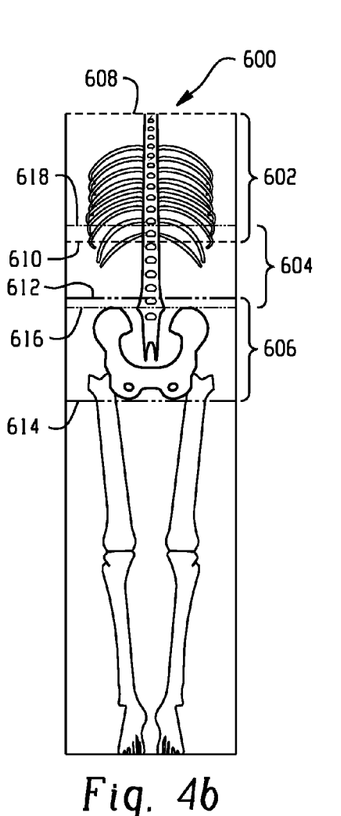

With reference to FIG. 4*a*, the pixels in each axial image slice are classified as air 650, soft tissue 652, or bone 654 as a function of x-ray attenuation. In scans using contrast agent, regions including contrast agent can be classified as bone, or may classified separately. The result is a graph or histogram in which the abscissa represents the slice number or location in the axial (z) direction and the ordinate represents the number of pixels plotted as a ratio to the mean for each class.

The partition of the chest 602, abdomen 604, and pelvis 606 is carried out in three main steps: identifying and segmenting the lungs, finding the pelvis and pubic bone, and identifying the diaphragm.

The lungs are identified using heuristics for finding air filled objects inside the body or partially inside the body (where lungs are cut off at the image border in the case of scans having a small field of view). Next, the lungs are segmented and the top and bottom borders of the lungs identified. The top 608 and bottom 610 borders of the chest region 602 are established slightly beyond the top and borders of the lungs.

The slices containing the pelvis and pubic bones are then identified on the histogram using feature detection techniques as are known to those skilled in the art. For studies including contrast the pelvis and pubic bones are preferably differentiated from the contrast for a more accurate identification. The top 612 and bottom 614 of the pelvic region 606 are established slightly beyond the pelvis and pubic bones, respectively.

The diaphragm is identified by evaluating the histogram for a falloff in body pixels located near the bottom of the lungs. The diaphragm and top of the pelvis bone define the top 618 and bottom 616 of the abdomen, respectively.

To identify the head and neck, the image is first preprocessed using feature detection to remove the bed and head holder. A histogram similar to FIG. 4b is generated, and the body area at each slice is also calculated. The interface between the head and neck is ascertained by evaluating the amount of bone and the body area.

Where one or more slices have not been assigned to a region of interest, the slices are preferably assigned to at least one region of interest near the slice. This avoids situations in which one or more slices are not assigned to a study, and thus not presented to the radiologist to review.

As will be appreciated, the above techniques can readily be extended to delineate between other anatomical regions, such as the torso and the legs, and the thighs and knees, and shins and spine.

Of course, other variations on the above techniques are also possible. Thus, for example, the one or both of the localizer scans 202, 302 may be omitted and the scan planning 206, 306 performed based on anatomical features or other information available to the operator. Similarly, the techniques may be performed using information generated by a device other than a CT scanner, such as a magnetic resonance (MR), single photon emission computed tomography (SPECT), positron emission tomography (PET), x-ray, or other scanner. The techniques are likewise not limited to human patients, and may be performed on other animate or on inanimate objects.

Moreover, the scanner need not be in communication with a computer information system. Also, the technique has been described as being performed on the scanner or computers associated with the scanner. As will be appreciated, all or a portion of techniques may be performed using computer systems or operator interfaces which are located remotely from the scanner but capable of receiving or exchanging data by way of a local or wide area computer network, the internet, wireless communications, portable physical storage media, a picture archiving and communications (PACS) system, or the like.

The invention has been described with reference to the preferred embodiments. Of course, modifications and alterations will occur to others upon reading and understanding the preceding description. It is intended that the invention be construed as including all such modifications and alterations insofar as they come within the scope of the appended claims or the equivalents thereof.

What is claimed is:

1. A method, comprising:
    obtaining a localizer scan of a patient;
    identifying first and second different anatomical volumes of the patient from the localizer scan;
    planning a signal scan covering the identified volumes using a first imaging protocol and a second different imaging protocol for each of the identified volumes, wherein each protocol is unique to anatomy of interest in the different anatomical volumes;
    obtaining, during the single scan, a single volumetric image data set that includes a plurality of images, wherein projection data reconstructed to generate the volumetric image data was generated by an imaging system operated to perform first and second different subscans of the patient during the single scan of the patient, wherein the first and second different subscans respectively are based on the first and the second different imaging protocols and cover the first and the second different volumes of a patient with respect to a long axis of the patient, and
    wherein a first subset of the plurality of the images includes data representative of the first volume of the patient and a second different subset of the images includes data representative of the second volume of the patient;
    obtaining the first imaging protocol;
    obtaining the second imaging protocol;
    using the first imaging protocol and the volumetric image data to generate a first set of images for the first volume of the patient with the first subset of the plurality of the images, wherein the first set of images is indicative of a first interior anatomy of the patient in the first volume of the patient;
    using the second imaging protocol and the volumetric image data to generate a second different set of images for the second volume of the patient with the second subset of the plurality of the images, wherein the second different set of images includes images indicative of a second interior anatomy of the patient in the second volume of the patient; and
    storing the first set of images with a first unique identifier and the second set of images with a second unique identifier in a computer readable storage medium.

2. The method of claim 1 wherein the first and second different volumes of the patient are non-overlapping volumes of the patient with respect to the long axis of the patient.

3. The method of claim 2 further comprising using the volumetric image data to identify the first and second subsets of the images in the volumetric image data when generating the first and second sets of images.

4. The method of claim 3 further comprising: classifying the volumetric image data into a plurality of categories, using morphological knowledge of the patient's anatomy, and evaluating the cross sectional area of the patient's anatomy.

5. The method of claim 3 wherein the first imaging protocol includes a first reconstruction protocol and the second imaging protocol includes a second reconstruction protocol.

6. The method of claim 5 wherein the first imaging protocol includes a first display protocol and the second imaging protocol includes a second display protocol.

7. The method of claim 1 wherein the localizer scan is a surview scan.

8. The method of claim 1 wherein the localizer scan is a volumetric scan.

9. The method of claim 1 wherein the first and second volumes of the patient respectively correspond to at least one of the lungs and the pelvis bone, the lungs and the diaphragm, or the pelvis bone and the diaphragm.

10. The method of claim 1 wherein the first and second sets of images each include an overview image of the first and second volumes of the patient and an identifier which uniquely identifies the set of images, and wherein the first and second volumes of the patient are indicated on the overview image.

11. The method of claim 1 wherein the first imaging protocol includes a first acquisition protocol and the second imaging protocol includes a second acquisition protocol.

12. The method of claim 1 further comprising notifying a computer information system that the first and second sets of images have been generated.

13. The method of claim 1, further comprising:
    classifying each pixel in the volumetric image data as one of air, bone or soft tissue;

using the first imaging protocol, the volumetric image data and the classification of the pixels to generate the first set of images; and using the second imaging protocol, the volumetric image data and the classification of the pixels to generate the second different set of images.

14. The method of claim 13, further comprising:

generating a histogram based on the classification;

using the first imaging protocol, the volumetric image data and the histogram to generate the first set of images; and using the second imaging protocol, the volumetric image data and the histogram to generate the second different set of images.

15. A method, comprising:

receiving, at an imaging system, two or more imaging requests to scan a patient with the imaging system, wherein the two or more imaging requests are for separate scans of different anatomical regions of the patient;

combining first and second imaging requests to scan a patient with the imaging system, wherein the first and second imaging requests are for separate scans of first and second different anatomical regions of the patient;

obtaining a localizer scan of the patient;

identifying the first and second different anatomical regions of the patient in the localizer scan;

planning a single scan covering the identified regions using a different protocol for each of the identified regions, wherein each protocol is unique to anatomy of interest in the different anatomical regions;

performing the single scan based on the plan, generating projection data indicative of the different anatomical regions;

reconstructing the projection data, generating a single set of volumetric image with images of the different anatomical regions;

identifying a first subset of the images of the single set of volumetric image as corresponding to the first anatomical region and a second subset of the images of the single set of volumetric image as corresponding to the second anatomical region; and creating and storing a first set of images with the first subset of the images and a second set of images with the second subset of the images.

* * * * *